United States Patent
Gers-Barlag et al.

(10) Patent No.: US 6,692,755 B2
(45) Date of Patent: Feb. 17, 2004

(54) EMULSIFIER-FREE FINELY DISPERSE SYSTEMS OF THE OIL-IN-WATER AND WATER-IN-OIL TYPE

(75) Inventors: Heinrich Gers-Barlag, Kummerfeld (DE); Anja Müller, Rümpel (DE)

(73) Assignee: Beiersdorf AG, Hamburg (DE)

( * ) Notice: Subject to any disclaimer, the term of this patent is extended or adjusted under 35 U.S.C. 154(b) by 34 days.

(21) Appl. No.: 10/132,751

(22) Filed: Apr. 25, 2002

(65) Prior Publication Data

US 2002/0160030 A1 Oct. 31, 2002

Related U.S. Application Data

(62) Division of application No. 09/396,557, filed on Sep. 15, 1999, now Pat. No. 6,579,529.

(30) Foreign Application Priority Data

Sep. 18, 1998 (DE) .......................... 198 42 732

(51) Int. Cl.[7] .......................... A61K 7/00; A61K 7/42; C01G 23/047
(52) U.S. Cl. .......................... 424/401; 424/59; 424/60; 514/937; 423/610
(58) Field of Search .......................... 424/401, 59, 60; 514/937; 423/610

(56) References Cited

U.S. PATENT DOCUMENTS

| | | |
|---|---|---|
| 5,420,118 A | 5/1995 | Alban et al. |
| 5,637,291 A | 6/1997 | Bara et al. |
| 5,643,555 A | 7/1997 | Collin et al. |
| 5,674,504 A | 10/1997 | Kauffmann |
| 5,725,844 A | 3/1998 | Gers-Barlag et al. |
| 5,728,391 A | 3/1998 | Ikeya et al. |
| 5,788,952 A | 8/1998 | Gers-Barlag et al. |
| 5,804,167 A | 9/1998 | Schonrock et al. |
| 5,833,951 A | 11/1998 | Artz et al. |
| 5,849,318 A | 12/1998 | Imai et al. |
| 5,965,066 A | 10/1999 | Koch et al. |
| 6,013,247 A | 1/2000 | Bara et al. |
| 6,579,529 B2 * | 6/2003 | Gers-Barlag et al. ........ 424/401 |

FOREIGN PATENT DOCUMENTS

| | | |
|---|---|---|
| DE | 33 01 123 A1 | 7/1983 |
| DE | 44 25 268 A1 | 1/1996 |
| DE | 44 29 468 A1 | 2/1996 |
| EP | 0 514 067 A1 | 11/1992 |
| EP | 0 610 926 A1 | 8/1994 |
| EP | 0 680 746 A | 8/1995 |
| EP | 0 683 662 B1 | 11/1995 |
| EP | 0 770 379 A2 | 5/1997 |
| EP | 0 787 483 A1 | 8/1997 |
| EP | 0 823 249 A1 | 1/1998 |
| GB | 2 113 116 A | 8/1993 |
| WO | WO 98/42300 | 10/1998 |
| WO | WO 98/42301 | 10/1998 |

* cited by examiner

*Primary Examiner*—Shelley A. Dodson
(74) *Attorney, Agent, or Firm*—Norris McLaughlin & Marcus

(57) ABSTRACT

Pickering emulsions, which are finely disperse systems of the water-in-oil or oil-in-water type, comprising
(1) an oil phase which contains a wax and/or an oil thickener,
(2) a water phase,
(3) at least one type of microfine particles which
 a) have an average particle size of less than 200 nm, which
 b) display both hydrophilic and lipophilic properties, i.e. which have amphiphilic character, and are dispersible both in water and in oil and which
 c) have optionally been coated on the surface,
(4) at least one type of non-amphiphilic metal oxide pigments and
(5) at most 0.5% by weight of one or more emulsifiers.

18 Claims, No Drawings

EMULSIFIER-FREE FINELY DISPERSE SYSTEMS OF THE OIL-IN-WATER AND WATER-IN-OIL TYPE

This applications is a divisional application of U.S. Ser. No. 09/396,557, filed on Sep. 15, 1999, now U.S. Pat. No. 6,579,529. issued on Jun. 2003.

The present invention relates to emulsifier-free finely disperse systems of the oil-in-water and water-in-oil type, preferably as cosmetic or dermatological preparations, in particular as cosmetic or dermatological light-protection preparations.

Emulsions are generally taken to mean heterogeneous systems which consist of two liquids which are immiscible or have only limited miscibility with one another, which are usually referred to as phases. In an emulsion, one of the two liquids is dispersed in the form of very fine droplets in the other liquid.

If the two liquids are water and oil and if oil droplets are finely dispersed in water, then this is an oil-in-water emulsion (O/W emulsion, e.g. milk). The basic character of an O/W emulsion is defined by the water. In a water-in-oil emulsion (W/O emulsion, e.g. butter), the principle is reversed, the basic character here being determined by the oil.

In order to achieve permanent dispersion of one liquid in another, emulsions in the traditional sense require the addition of an interface-active substance (emulsifier). Emulsifiers have an amphiphilic molecular structure, consisting of a polar (hydrophilic) and a nonpolar (lipophilic) molecular moiety, which are spatially separate from one another. In simple emulsions, finely disperse droplets of one phase, surrounded by an emulsifier shell, (water droplets in W/O emulsions or lipid vesicles in O/W emulsions) are present in the second phase. Emulsifiers lower the interfacial tension between the phases by positioning themselves at the interface between two liquids. At the phase boundary, they form oil/water interfacial films, which prevent irreversible coalescence of the droplets. Emulsions are frequently stabilized using emulsifier mixtures.

Traditional emulsifiers can, depending on their hydrophilic molecular moiety, be divided into ionic (anionic, cationic and amphoteric) and nonionic:

The most well-known example of an anionic emulsifier is soap, which is usually the term used for the water-soluble sodium or potassium salts of saturated or unsaturated higher fatty acids.

Important examples of cationic emulsifiers are quaternary ammonium compounds.

The hydrophilic molecular moiety of nonionic emulsifiers frequently consists of glycerol, polyglycerol, sorbitans, carbohydrates and polyoxyethylene glycols, and, in most cases, is linked to the lipophilic molecular moiety via ester and ether bonds. The lipophilic molecular moiety usually consists of fatty alcohols, fatty acids or isofatty acids.

By varying the structure and the size of the polar and nonpolar molecular moiety, the lipophilicity and hydrophilicity of emulsifiers can be varied within wide limits.

A decisive factor for the stability of an emulsion is the correct choice of emulsifiers. The characteristics of all substances present in the system are to be taken into consideration here. In the case of, for example, skincare emulsions, polar oil components and, for example, UV filters lead to instability. As well as the emulsifiers, therefore, other stabilizers are also used which, for example, increase the viscosity of the emulsion and/or act as protective colloid.

Emulsions are an important type of product in the field of cosmetic and/or dermatological preparations.

Cosmetic preparations are essentially used for skin care. The main aim of skin care in the cosmetics sense is to strengthen or rebuild the skin's natural function as a barrier against environmental influences (e.g. dirt, chemicals, microorganisms) and against the loss of endogenous substances (e.g. water, natural fats, electrolytes). If this function becomes impaired, increased resorption of toxic or allergenic substances or attack by microorganisms may result, leading to toxic or allergic skin reactions.

Another aim of skin care is to compensate for the loss by the skin of lipids and water caused by daily washing. This is particularly important if the natural regeneration ability is inadequate. Furthermore, skincare products should protect against environmental influences, in particular against sun and wind, and delay skin ageing.

Medicinal topical compositions usually comprise one or more medicaments in an effective concentration. For the sake of simplicity, in order to distinguish clearly between cosmetic and medicinal use and corresponding products, reference is made to the legal provisions in the Federal Republic of Germany (e.g. Cosmetics Directive, Foods and Drugs Act).

The use of customary emulsifiers in cosmetic or dermatological preparations is in itself acceptable. Nevertheless, emulsifiers, like ultimately any chemical substance, may in certain circumstances cause allergic reactions or reactions based on oversensitivity of the user.

For example, it is known that certain light dermatoses are triggered by certain emulsifiers, but also by various fats and simultaneous exposure to sunlight. Such light dermatoses are also called "Mallorca acne". There has thus been no lack of attempts to reduce the amount of customary emulsifiers to a minimum, in the ideal case even to zero.

A reduction in the required amount of emulsifier can, for example, be achieved by taking advantage of the fact that very finely divided solid particles have an additional stabilizing action. The solid substance accumulates at the oil/water phase boundary in the form of a layer, as a result of which coalescence of the disperse phases is prevented. It is not the chemical properties of the solid particles which are of fundamental importance here, but the surface properties.

Around 1910, Pickering prepared paraffin/water emulsions which were stabilized merely by the addition of various solids, such as basic copper sulphate, basic iron sulphate or other metal sulphates. This type of emulsion is thus also referred to as a Pickering emulsion.

The original forms of Pickering emulsions initially surfaced, as it were, as undesired secondary effects in a variety of industrial processes, such as, for example, in secondary oil recovery, the extraction of bitumen from tar sand and other separation processes involving two immiscible liquids and fine, dispersed solid particles. These are generally W/O emulsions which are stabilized by mineral solids. Accordingly, investigation of corresponding systems, such as, for example, the oil/water/soot or oil/water/slate dust systems was initially the focus of research activity.

Basic experiments have shown that one characteristic of a Pickering emulsion is that the solid particles are arranged at the interface between the two liquid phases, where they form, as it were, a mechanical barrier against the combining of the liquid droplets.

It is a relatively new technical development to use Pickering emulsions as a base for cosmetic or dermatological preparations.

One way of achieving solids stabilization in the sense of a pickering emulsion in a cosmetic or dermatological preparation is, according to May-Alert (*Pharmazie in unserer Zeit* [*Pharmacy in our time*], Vol. 15, 1986, No. 1, 1-7) for example, to use emulsifier mixtures which comprise both anionic and cationic surfactants. Since mixing anionic and cationic surfactants always results in the precipitation of insoluble, electroneutral compounds, deliberate precipitation of these neutral surfactants in the oil/water interface makes it possible to achieve additional solids stabilization.

European Laid-open Specification 0 686 391, moreover, describes emulsions of the water-in-oil type which are free from surface-active substances and are stabilized only by solids. Stabilization is achieved here using spherical polyalkylsilsesquioxane particles which have a diameter of from 100 nm up to 20 $\mu$m. These emulsions can be referred to as Pickering emulsions according to that mentioned above.

Pickering emulsions are stabilized by the use of suitable solids or pigments. However, Pickering emulsions of the prior art in general have the disadvantage that they only act unsatisfactorily against UV light, in particular against UV-A light, since pigments which are particularly suitable for the stabilization of this type of emulsion in general have an inadequate light-protection action.

The harmful action of the ultraviolet part of the solar radiation on the skin is generally known. Depending on its particular wavelength, the rays have various actions on the organ skin: the so-called UV-C radiation having a wavelength which is less than 290 nm is absorbed by the ozone layer in the earth's atmosphere and therefore has no physiological importance. However, rays in the range between 290 nm and 320 nm, the so-called UV-B range, cause erythema, simple sunburn or even burns which are more or less severe. The narrow range around 308 nm is indicated as a maximum of the erythema activity of sunlight.

For a long time, it has been falsely assumed that the long-wave UV-A radiation having a wavelength between 320 nm and 400 nm only has a negligible biological action and that, accordingly, the UV-B rays are responsible for most light damage to the human skin. Since then, however, it has been confirmed by numerous studies that UV-A radiation is far more hazardous than UV-B radiation with respect to the triggering of photodynamic, especially phototoxic, reactions and chronic changes in the skin. The harmful effect of the UV-B radiation can also be further increased by UV-A radiation.

Preventive protection against UV radiation, for example by application of sunscreen filter substances in the form of a cosmetic or dermatological formulation to the skin, is therefore of fundamental importance. In particular, this also applies to formulations whose main purpose is not protection from sunlight, but which in general are applied to body parts which are customarily exposed to daylight, such as, for example, face- and bodycare preparations.

The object was therefore to remedy the disadvantages of the prior art. In particular, the intention was to provide cosmetic and dermatological bases for cosmetic and dermatological preparations which are characterized by good skin tolerability and high UV protection performance, in particular high UV-A protection performance.

In addition, an object of the present invention was to provide products with the widest possible variety of applications. For example, the intention was to provide bases for preparation forms such as cleansing emulsions, facecare and bodycare preparations, but also distinctly medicinal-pharmaceutical presentation forms, for example preparations against acne and other skin conditions.

It was surprising and in no way predictable by the person skilled in the art that Pickering emulsions, which are finely disperse systems of the water-in-oil or oil-in-water type, comprising (1) an oil phase,
(2) a water phase,
(3) at least one type of microfine particles which
   a) have an average particle size of less than 200 nm, which
   b) display both hydrophilic and lipophilic properties, i.e. which have amphiphilic character, and are dispersible both in water and in oil and which
   c) have optionally been coated on the surface,
(4) at least one type of non-amphiphilic metal oxide pigments and
(5) at most 0.5% by weight of one or more emulsifiers, overcome the disadvantages of the prior art.

According to the invention, it is particularly advantageous if the preparations comprise significantly less than 0.5% by weight of one or more emulsifiers or are even entirely free from emulsifiers.

The preparations according to the invention are extremely satisfactory preparations in every respect which are particularly suitable to serve as a base for preparation forms having a variety of applications. Moreover, the preparations according to the invention are distinguished by an excellent skin tolerability.

It was furthermore surprising that preparations according to the invention have a higher efficacy against UV radiation, in particular a higher UV-A protection performance, than customary sunscreen formulations based on Pickering emulsions.

While preparations of the prior art having a pigment content of as little as 1% by weight produce a dull feel following their application to the skin, which increases further with higher pigment concentrations, the preparations according to the invention, surprisingly, do not leave a dry or dull impression on the skin, but on the contrary exhibit excellent cosmetic properties.

Although the prior art recognizes, in addition to Pickering emulsions, emulsifier-free, finely disperse cosmetic or dermatological preparations, which are generally referred to as hydrodispersions and which are dispersions of a liquid, semisolid or solid inner (discontinuous) lipid phase in an outer aqueous (continuous) phase, the prior art was unable to point the way to the present invention.

In the case of hydrodispersions of a liquid lipid phase in an external aqueous phase, the stability can be guaranteed, for example, by building up a gel structure in the aqueous phase, in which the lipid droplets are stably suspended.

German Laid-open Specification 44 25 268 describes stable finely disperse, emulsifier-free cosmetic or dermatological preparations of the oil-in-water type, which in addition to an oil and a water phase contain one or more thickeners from the group consisting of the acrylic acid polymers, polysaccharides and their alkyl ethers, where a lowering of interfacial tension may not be measurable for these thickeners.

Based on similar hydrodispersions, German Laid-open specification 43 03 983 discloses cosmetic or dermatological sunscreen formulations which are essentially free of emusifiers, inorganic micropigments which serve as UV filter substances being incorporated into the lipid phase of the hydrodispersion.

O/W Pickering emulsions within the meaning of the present invention, however, are obtainable by first dispersing amphiphilic particles according to the invention suitable for the preparation of O/W Pickering emulsions in the water phase and then combining the water phase with the fatty phase. W/O Pickering emulsions according to the invention, however, are obtainable by dispersing amphiphilic particles according to the invention suitable for the preparation of W/O Pickering emulsions in the fatty phase.

The non-amphiphilic metal oxide pigments selected from the group consisting of the oxides of titanium ($TiO_2$), zinc (ZnO), iron (e.g. $Fe_2O_3$), zirconium ($ZrO_2$), silicon ($SiO_2$), manganese (e.g. MnO), aluminium ($Al_2O_3$), cerium (e.g. $Ce_2O_3$), mixed oxides of the corresponding metals and mixtures of such oxides are advantageous within the meaning of the present invention. Non-amphiphilic pigments based on $TiO_2$ are particularly preferred.

The non-amphiphilic pigments are advantageously present according to the invention in hydrophobic form, i.e. in that they have a water-repellant treatment on the surface. This surface treatment can consist in providing the pigments with a thin hydrophobic layer according to processes known per se. Advantageous hydrophobic $TiO_2$ pigments are obtainable, for example, from Degussa under the trade name T 805 (CAS-No. 100209-12-9, ex 13463-67-7).

A further advantageous hydrophobic coating consists of aluminium hydroxide or hydrated aluminium oxide (also: alumina, CAS No.: 1333-84-2), to which stearic acid is then applied. It is moreover also preferred to apply other hydrophobic coatings to metal oxide particles pretreated with alumina, such as, for example, polyorganosiloxanes. Advantageous non-amphiphilic titanium dioxide pigments coated with alumina and stearic acid are obtainable, for example, from Kemira under the trade name UV Titan M160.

According to the invention, advantageous dispersions are furthermore those of ultrafine titanium dioxide in oils or oily titanium dioxide suspensions, e.g. titanium dioxide in caprylic/capric triglyceride, a mixture of triglycerides mainly of caprylic acid [$CH_3(CH_2)_6COOH$] and of capric acid [$CH_3(CH_2)_8COOH$]. The oily titanium dioxide suspensions obtainable from Solaveil under the trade name Tioveil TG, for example, are preferred.

Within the meaning of the present invention, the non-amphiphilic metal oxide pigments are furthermore preferably selected from the group consisting of the hydrophilic or hydrophilically coated pigments. The surface treatment can consist in providing the pigments with a thin hydrophilic layer by processes known per se.

Aqueous dispersions of hydrophilic titanium oxide pigments, for example, which can also contain other constituents, e.g. preserving constituents, such as, for example, propylene glycol, are furthermore advantageous. The aqueous titanium dioxide suspensions obtainable from Solaveil under the trade name Tioveil AQ, for example, are preferred.

The total amount of non-amphiphilic metal oxide pigments, in particular hydrophobic micropigments in the finished cosmetic or dermatological preparations is advantageously chosen to be less than 20% by weight, preferably between 0.5 and 10.0% by weight, based on the total weight of the preparations.

It is also advantageous, although not obligatory, for the Pickering emulsions according to the invention to comprise auxiliaries which can additionally increase the stability of these preparations, for example substances (one or more) which are chosen from the group of waxes and/or oil thickeners, of hydrocolloids and of electrolytes.

It is also advantageous for the Pickering emulsions according to the invention to comprise auxiliaries which can contribute to reducing or preventing a dull or dry feel on the skin following their application, where it is possible that the main purpose of these substances is a different one. Preferably, these substances are, for example, chosen from the group of unsymmetrically substituted s-triazine derivatives, cyclodextrins, film formers and polymeric moisturizers, it being possible for these substances to be present either individually or in a mixture.

The cosmetic properties of the Pickering emulsions according to the invention can additionally, for example, be further improved by also using oils in the oil phase which have a viscosity of less than 30 mPa.s, in particular of less than 20 mPa.s (determined using a rheometer from Contraves (Rheomat 108E) at a shear gradient of 500/s and a temperature of 25° C.).

Microfine amphiphilic particles:

The amphiphilic character of the microfine particles according to the invention is evident, for example, from the fact that they are dispersible both in water and in oil.

It is advantageous to choose the average particle diameter of the amphiphilic particles to be between 1 nm and 200 nm, particularly advantageously between 5 nm and 100 nm.

It is also advantageous to choose the concentration of all amphiphilic particles according to the invention to be greater than 0.1% by weight, particularly advantageously between 0.1% by weight and 30% by weight, based on the total weight of the preparations.

For the purposes of the present invention, advantageous particles are all amphiphilic particles which are suitable for stabilizing Pickering W/O emulsions or Pickering O/W emulsions. It is essentially insignificant for the present invention in which of the potentially naturally occurring modifications the particles are present.

To stabilize the Pickering emulsions, preference is given to using untreated, virtually pure pigment particles, for example those which can be used as dyes in the food industry. Examples of advantageous pigments are the zinc oxide pigments available from Merck which are available under the trade names Zinkoxid neutral from Haarmann & Reimer or NanoX from Harcros Chemical Group.

For the purposes of the present invention, Pickering emulsions are likewise advantageously stabilized by inorganic pigments which have been surface-treated ("coated") to repel water, where at the same time the intention is to form or retain the amphiphilic character. This surface-treatment can, for example, consist in providing the pigments partially with a thin hydrophobic layer or else almost completely with an amphiphilic layer by processes known per se.

One such process, which is described below using titanium dioxide as an example, consists in, for example, producing the hydrophobic surface layer according to the following reaction

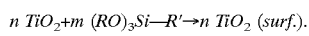

n and m are arbitrary stoichiometric parameters, and R and R' are the desired organic radicals. Particularly advantageous are $TiO_2$ pigments, for example those coated with aluminium stearate, available under the trade name MT 100 T from TAYCA.

A further advantageous coating of the inorganic pigments consists of dimethylpolysiloxane (also: dimethicone), a mixture of completely methylated, linear siloxane polymers which are terminally blocked with trimethylsiloxy units. For the purposes of the present invention, particularly advantageous pigments are zinc oxide pigments which are coated in this way.

Also advantageous is a coating of the amphiphilic pigments with a mixture of dimethylpolysiloxane, in particular dimethylpolysiloxane having an average chain length of from 200 to 350 dimethylsiloxane units, and silica gel, which is also referred to as simethicone. It is particularly advantageous if the amphiphilic pigments have been additionally coated with aluminium hydroxide or hydrated aluminium oxide (also: alumina, CAS No.: 1333-84-2). Particularly advantageous are titanium dioxides which have been coated with simethicone and alumina, it being possible for the coating to also comprise water. One example thereof is the titanium dioxide available under the trade name Eusolex T2000 from Merck.

For the purposes of the present invention it is also advantageous to use a mixture of different pigment types either within a crystal, for example as mixed iron oxide, or by combination of two or more pigment types within a preparation.

The Pickering emulsions are also preferably stabilized by boron nitride particles, for example by the boron nitrides listed below:

| Trade name | Available from |
|---|---|
| Boron Nitride Powder | Advanced Ceramics |
| Boron Nitride Powder | Sintec Keramik |
| Ceram Blanche | Kawasaki |
| HCST Boron Nitride | Stark |
| Très BN ® | Carborundum |
| Wacker-Bornitrid BNP | Wacker-Chemie |

It is advantageous to choose the average particle diameter of the boron nitride particles used to be less than 20 μm, particularly advantageously less than 15 μm. For the purposes of the present invention, Pickering emulsions are likewise advantageously stabilized by boron nitride particles which have been surface-treated ("coated") to repel water, where at the same time the intention is to form or retain the amphiphilic character.

An advantageous coating of the boron nitride particles consists of dimethylpolysiloxane (dimethicone). The boron nitride particles treated with dimethicone and available from Carborundum under the trade name Très BN® UHP 1106 are advantageous, for example.

Also advantageous is a coating of the boron nitride particles with polymethylhydrogensiloxane, a linear polysiloxane which is also referred to as methicone. Advantageous boron nitride particles treated with methicone are, for example, those available from Carborundum under the trade name Très BN® UHP 1107.

It is also advantageous to stabilize the Pickering emulsions according to the invention using microfine polymer particles.

For the purposes of the present invention, examples of advantageous microfine polymer particles are polycarbonates, polyethers, polyethylenes, polypropylenes, polyvinyl chloride, polystyrene, polyamides, polyacrylates and the like.

Advantageous according to the invention are, for example, microfine polyamide particles which are available under the trade name SP-500 from TORAY. Also advantageous are polyamide 6 (also: nylon 6) and polyamide 12 (also: nylon 12) particles. Polyamide 6 is the polyamide formed from ε-aminocaproic acid (6-aminohexanoic acid) or ε-caprolactam [poly(ε-caprolactam)], and polyamide 12 is a poly(ε-laurolactam) from ε-laurolactam. For the purposes of the present invention, Orgasol® 1002 (polyamide 6) and Orgasol® 2002 (polyamide 12) from ELF ATOCHEM, for example, are advantageous.

Other advantageous polymer particles are microfine polymethacrylates. Such particles are available, for example, under the trade name POLYTRAP® from DOW CHEMICAL.

It is particularly advantageous, but not obligatory, if the microfine polymer particles used have been surface-coated. This surface-treatment can consist in providing the pigments with a thin hydrophilic layer by processes known per se. Advantageous coatings consist, for example, of $TiO_2$, $ZrO_2$ or also other polymers, such as, for example, polymethyl methacrylate.

Particularly advantageous microfine polymer particles for the purposes of the present invention are also obtainable by the process, described in U.S. Pat. No. 4,898,913, for the hydrophilic coating of hydrophobic polymer particles.

It is advantageous to choose the average particle diameter of the microfine polymer particles used to be less than 100 μm, particularly advantageously less than 50 μm. In this connection, it is essentially insignificant in which form (platelets, rods, spherules, etc.) the polymer particles used are present.

In addition, it is advantageous to stabilize the Pickering emulsions according to the invention using modified polysaccharides.

For the purposes of the present invention, modified polysaccharides are, for example, obtainable by reaction of starch with mono-, bi- or polyfunctional reagents or oxidizing agents in reactions which proceed in a largely polymer-analogous manner.

Such reactions are based essentially on modifications of the hydroxyl groups of the polyglucans by etherification, esterification or selective oxidation. This produces, for example, so-called starch ethers and starch esters of the general structural formula Structural formula (I)

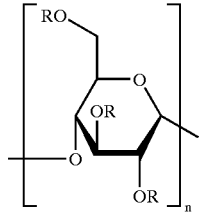

in which R can, for example, be a hydrogen and/or an alkyl and/or an aralkyl radical (in the case of starch ethers) or a hydrogen and/or an organic and/or inorganic acid radical (in the case of starch esters). Starch ethers and starch esters are advantageous, modified polysaccharides for the purposes of the present invention.

Particularly advantageous starch ethers are, for example, those which are obtainable by etherification of starch with tetramethylolacetylenediurea and which are referred to as non-mucilaginous starch (nonswelling starch).

Also particularly advantageous are starch esters and salts thereof, for example the sodium and/or aluminium salts of half-esters of starch which have low degrees of substitution, in particular sodium starch n-octenyl succinate of the structural formula (II) in which R is characterized by the following structure

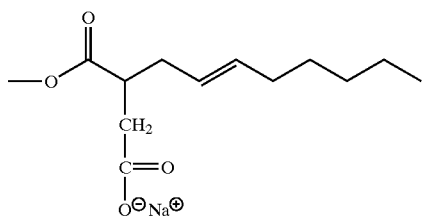

and which is available, for example, under the trade name Amiogum® 23 from CERESTAR, and aluminium starch octenyl succinates, in particular those available under the trade names Dry Flo® Elite LL and Dry Flo® PC from CERESTAR.

It is advantageous to choose the average particle diameter of the modified polysaccharide used to be less than 20 μm, particularly advantageously less than 15 μm.

The list of given modified polysaccharides which are able to stabilize Pickering emulsions according to the invention is of course not intended to be limiting. For the purposes of the present invention, modified polysaccharides are obtainable in a large number of ways known per se, both of a chemical and a physical nature.

The abovementioned amphiphilic particles are outstandingly suitable both for the stabilization of W/O Pickering emulsions and for the stabilization of O/W Pickering emulsions. Microfine particles according to the invention are mentioned below which advantageously particularly stabilize one of the two emulsion types W/O or O/W.

W/O Pickering emulsions:

The water phase proportion in the W/O Pickering emulsions according to the invention is preferably chosen from the range of from 0.5 to 75% by weight, based on the total weight of the formulations.

Also particularly advantageous for stabilizing W/O Pickering emulsions are magnesium silicates (also: talc), for example those available under the trade name Talkum Micron from Grolmann.

O/W Pickering emulsions

The fatty phase proportion of the O/W Pickering emulsions according to the invention is preferably chosen from the range of 0.5 to 75% by weight, based on the total weight of the formulations.

Particularly advantageous for the stabilization of O/W Pickering emulsions within the meaning of the present invention are also untreated, almost pure pigment particles, for example titanium dioxide pigments, in particular those which are obtainable from Kronos Titan under the trade name KRONOS® 1171 ($TiO_2$).

O/W Pickering emulsions within the meaning of the present invention are furthermore particularly advantageously stabilized by amphiphilic metal oxide particles which are coated with aluminium hydroxide and/or silicon dioxide. Advantageous embodiments are, for example, titanium dioxide particles which are obtainable from Merck under the name EUSOLEX® TA.

It is also advantageous, but not obligatory, to combine the amphiphilic particles according to the invention with other particles which may or may not also be able to contribute to the stabilization of the Pickering emulsions.

Such particles are, for example, titanium dioxide pigments which have been coated with octylsilanol, and/or silicon dioxide particles which have been surface-treated to repel water. Suitable silicon dioxide particles are, for example, spherical polyalkylsilsesquioxane particles, as mentioned in European Laid-open Specification 0 686 391. Such polyalkylsilsesquioxane particles are available, for example, under the trade names Aerosil R972 and Aerosil 200V from Degussa. Suitable titanium dioxide particles are available under the trade name T805, also from Degussa.

The Pickering emulsions according to the invention can be used as bases for cosmetic or dermatological formulations. These can have the customary composition and be used, for example, for the treatment and care of the skin, as lipcare products, as make-up products or make-up remover products in decorative cosmetics or as light protection preparations. For use, the cosmetic and dermatological preparations according to the invention are applied to the skin in sufficient amounts in the manner customary for cosmetics.

Accordingly, for the purposes of the present invention, cosmetic or topical dermatological compositions may, depending on their structure, be used, for example, as skin-protection creams, cleansing milks, sunscreen lotions, nourishing creams, day creams or night creams, etc. In some instances, it is possible and advantageous to use the compositions according to the invention as bases for pharmaceutical formulations.

The cosmetic and dermatological preparations according to the invention can comprise cosmetic auxiliaries, as are customarily used in such preparations, e.g. preservatives, bactericides, perfumes, antifoams, dyes, pigments which have a colouring effect, thickeners, emollients, moisturizers and/or humectants, fats, oils, waxes and other customary constituents of a cosmetic or dermatological formulation, such as alcohols, polyols, polymers, foam stabilizers, electrolytes, organic solvents or silicone derivatives.

Pickering emulsions according to the invention may also contain thickeners to improve the tactile properties of the emulsion.

In particular, the Pickering emulsions according to the invention may also comprise antioxidants. According to the invention, favourable antioxidants which can be used are any antioxidants suitable or conventional for cosmetic and/or dermatological applications.

The antioxidants are advantageously chosen from the group consisting of amino acids (e.g. glycine, histidine, tyrosine, tryptophan) and derivatives thereof, imidazoles, (e.g. urocanic acid) and derivatives thereof, peptides, such as D,L-carnosine, D-carnosine, L-carnosine and derivatives thereof (e.g. anserine), carotenoids, carotenes (e.g. α-carotene, β-carotene, lycopene) and derivatives thereof, chlorogenic acid and derivatives thereof, lipoic acid and derivatives thereof (e.g. dihydrolipoic acid), aurothioglucose, propylthiouracil and other thiols (e.g. thioredoxin, glutathione, cysteine, cystine, cystamine and the glycosyl, N-acetyl, methyl, ethyl, propyl, amyl, butyl and lauryl, palmitoyl, oleyl, γ-linoleyl, cholesteryl and glyceryl esters thereof) and the salts thereof, dilauryl thiodipropionate, distearyl thiodipropionate, thiodipropionic acid and derivatives thereof (esters, ethers, peptides, lipids, nucleotides, nucleosides and salts) and sulphoximine compounds (e.g. buthionine sulphoximines, homocysteine sulphoximine, buthionine sulphones, penta-, hexa-, heptathionine sulphoximine) in very low tolerated doses (e.g. pmol to μmol/kg), and also (metal) chelating agents (e.g. α-hydroxy fatty acids, palmitic acid, phytic acid, lactoferrin), α-hydroxy acids (e.g. citric acid, lactic acid, malic acid), humic acid, bile acid, bile extracts, bilirubin, biliverdin, EDTA, EGTA and derivatives thereof, unsaturated fatty acids and derivatives thereof (e.g. γ-linolenic acid, linoleic acid, oleic acid), folic acid and derivatives thereof, ubiquinone and ubiquinol and derivatives thereof, vitamin C and derivatives (e.g. ascorbyl palmitate, Mg ascorbyl phosphate, ascorbyl acetate), tocopherols and derivatives (e.g. vitamin E acetate), vitamin A and derivatives (vitamin A palmitate) and coniferyl benzoate of benzoin resin, rutinic acid and derivatives thereof, α-glycosylrutin, ferulic acid, furfurylideneglucitol, carnosine, butylated hydroxytoluene, butylated hydroxyanisole, nordihydroguaiac acid, nordihydroguaiaretic acid, trihydroxybutyrophenone, uric acid and derivatives thereof, mannose and derivatives thereof, zinc and derivatives thereof (e.g. ZnO, $ZnSO_4$), selenium and its derivatives (e.g. selenomethionine), stilbenes and their derivatives (e.g. stilbene oxide, trans-stilbene oxide), and the derivatives (salts, esters, ethers, sugars, nucleotides, nucleosides, peptides and lipids) of said active substances which are suitable according to the invention.

The amount of the abovementioned antioxidants (one or more compounds) in the preparations according to the invention is preferably from 0.001 to 30% by weight, particularly preferably from 0.05–20% by weight, in particular 1–10% by weight, based on the total weight of the preparation.

If vitamin E and/or derivatives thereof are used as the antioxidant or antioxidants, their respective concentrations are advantageously chosen from the range of 0.001–10% by weight, based on the total weight of the formulation.

If vitamin A or vitamin A derivatives or carotenes or derivatives thereof are used as the antioxidant or antioxidants, their respective concentrations are advantageously chosen from the range of 0.001–10% by weight, based on the total weight of the formulation.

Cosmetic and dermatological preparations which are in the form of a sunscreen are also favourable. These preferably comprise at least one UV-A filter substance and/or at least one UV-B filter substance.

For the purposes of the present invention, it is, however, also advantageous to provide such cosmetic and dermatological preparations whose main purpose is not protection against sunlight, but which nevertheless additionally comprise substances which protect against UV. For example, UV-A and UV-B filter substances are commonly incorporated into day creams.

The preparations according to the invention can advantageously comprise other substances which absorb UV radiation in the UV-B range, the total amount of filter substances being, for example, from 0.1% by weight to 30% by weight, preferably from 0.5 to 10% by weight, in particular from 1.0 to 6.0% by weight, based on the total weight of the preparations, in order to provide cosmetic preparations which protect the hair and/or the skin from the whole of ultraviolet radiation.

If the emulsions according to the invention contain UV-B filter substances, these can be oil-soluble or water-soluble. Advantageous oil-soluble UV-B filters according to the invention are, for example:

- 3-benzylidenecamphor derivatives, preferably 3-(4-methylbenzylidene)camphor, 3-benzylidenecamphor;
- 4-aminobenzoic acid derivatives, preferably 2-ethylhexyl 4-dimethylaminobenzoate, amyl 4-dimethylaminobenzoate;
- esters of cinnamic acid, preferably 2-ethylhexyl 4-methoxycinnamate, isopentyl 4-methoxycinnamate;
- esters of salicylic acid, preferably 2-ethylhexyl salicylate, 4-isopropylbenzyl salicylate, homomenthyl salicylate,
- derivatives of benzophenone, preferably 2-hydroxy-4-methoxybenzophenone, 2-hydroxy-4-methoxy-4'-methylbenzophenone, 2,2'-dihydroxy-4-methoxybenzophenone;
- esters of benzalmalonic acid, preferably di(2-ethylhexyl) 4-methoxybenzalmalonate,
- triazine derivatives which are symmetrical with respect to the $C_3$ axis of the triazine parent structure, preferably tris(2-ethylhexyl) 4,4',4"-(1,3,5-triazine-2,4,6-triyltriimino)trisbenzoate,
- benzotriazole derivatives, preferably 2,2'-methylenebis(6-(2H-benzotriazol-2-yl)-4-(1,1,3,3,-tetramethylbutyl)phenol)
- and UV filters bonded to polymers.

Examples of advantageous water-soluble UV-B filters are:
- salts of 2-phenylbenzimidazol-5-sulphonic acid, such as its sodium, potassium or triethanolammonium salts, and the sulphonic acid itself;
- sulphonic acid derivatives of benzophenones, preferably 2-hydroxy-4-methoxybenzophenone-5-sulphonic acid and salts thereof;
- sulphonic acid derivates of 3-benzylidenecamphor, such as, for example, 4-(2-oxo-3-bornylidenemethyl)benzenesulphonic acid, 2-methyl-5-(2-oxo-3-bornylidene-methyl)sulphonic acid and salts thereof.

The list of UV-B filters mentioned which can be used in the Pickering emulsions according to the invention should, of course, be non-limiting.

It can also be advantageous to use other UV-A filters which hitherto have customarily been contained in cosmetic preparations in Pickering emulsions according to the invention. These substances are preferably derivatives of dibenzoylmethane, in particular 1-(4'-tert-butylphenyl)-3-(4'-methoxyphenyl)propane-1,3-dione and 1-phenyl-3-(4'-isopropylphenyl)propane-1,3-dione.

Other advantageous UV-A filter substances are phenylene-1,4-bis(2-benzimidazyl)-3,3'-5,5'-tetrasulphonic acid:

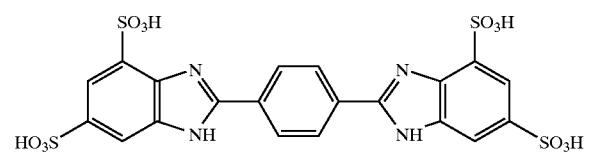

and its salts, particularly the corresponding sodium, potassium or triethanolammonium salts, in particular the bis-sodium salt of phenylene-1,4-bis(2-benzimidazyl)-3,3'–5,5'-tetrasulphonic acid:

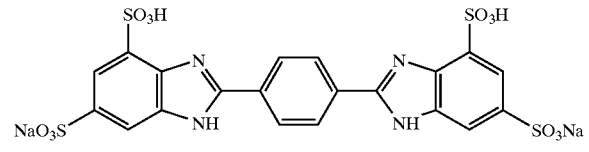

and 1,4-di(2-oxo-10-sulfo-3-bornylidenemethyl)benzene and salts thereof (particularly the corresponding 10-sulfato compounds, in particular the corresponding sodium, potassium or triethanolammonium salt), which is also referred to as benzene-1,4-di(2-oxo-3-bornylidenemethyl-10-sulphonic acid) and is characterized by the following structure:

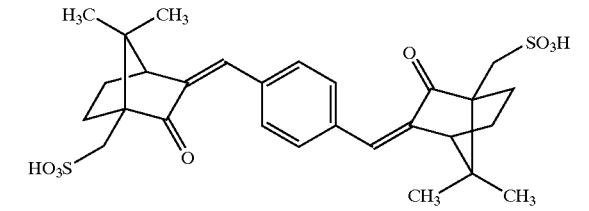

Preparations which contain other UV-A filters are also a subject of the invention. The amounts used for the UV-B combination can be employed.

The examples below serve to illustrate the present invention without limiting it. The numerical values in the examples are percentages by weight, based on the total weight of the respective preparations.

EXAMPLES

| | 1 W/O | 2 W/O | 3 W/O | 4 O/W | 5 O/W | 6 O/W |
|---|---|---|---|---|---|---|
| Amphiphilic titanium dioxide (Eusolex T2000) | 2 | 4 | 6 | 3 | 5 | 2 |
| Amphiphilic zinc oxide | 5 | | 4 | | | 4 |
| Non-amphiphilic titanium dioxide (Titandioxid T805) | | | 2 | | 2 | |
| Non-amphiphilic titanium dioxide (Sperse ® TN) | 5 | | | | | 2 |
| Non-amphiphilic titanium dioxide (UV Titan M160) | | 2 | | | | |
| Non-amphiphilic titanium dioxide (Tioveil TG) | | | | 2 | | |
| Silica (Aerosil R972) | | 1 | 0.5 | | | |
| Talc (Talkum Micron) | | 0.5 | | | | |
| Boron nitride | | 2 | | | | |
| Sodium maize starch n-octenylsuccinate | | | | 0.5 | | 1 |
| Hydroxystearyl hydroxy-stearate (Elfacos C26) | 2 | | 2 | | | |
| C$_{20-40}$-alkyl stearate (Kesterwachs K82) | 1 | 1 | | | | |
| C$_{16-38}$-alkylhydroxy-stearolyl stearate (Kesterwachs K80P) | | 2 | | 3 | | |
| Behenoxy dimethicone (Abil Wax 2440) | | | 5 | | | |
| Polyisobutene (Rewopal PIB 1000) | 5 | | 5 | | | |
| Caprylic/capric triglyceride | 5 | 5 | 5 | 15 | 20 | 20 |
| Octyldodecanol | 5 | | 5 | 15 | | 15 |
| Mineral oil | 10 | | | 10 | | 20 |
| Butylene glycol caprylate/caprate | | 10 | 10 | | 20 | 7 |
| C$_{12-15}$-alkyl benzoate | 10 | 10 | 10 | 5 | 15 | |
| Dimethicone | | 2 | 3 | | | |
| Dicaprylyl ether (Cetiol OE) | | | | 5 | | |
| Hydrogenated polyiosbutene (Polysynlan) | 2 | | | | | |
| Methylbenzylidenecamphor | | 3 | | | 4 | |
| Octyltriazone | | 1 | | | 4 | |
| Dibenzoylmethane | | 2 | | | 2 | |
| Dioctylbutamidotriazone (UVASORB HEB) | | 2 | | | | |
| Preservative | 0.5 | 0.5 | 0.5 | 0.5 | 0.5 | 0.5 |
| Glycerol | 5 | 10 | 3 | 5 | 5 | 5 |
| Biosaccharide gel (Fucogel 1000) | | | | 5 | | |
| Hyaluronic acid | | | | | 0.5 | |
| NaCl | 1 | | 1 | | | |
| MgSO$_4$ | | 0.5 | | | | |
| Phenylbenzimi-dazolesulphonic acid | | 1 | | | 2 | |
| Carbomer (Carbopol 981) | | | | 0.1 | | |
| Xanthan gum | | | | 0.3 | | |
| Cellulose gum (Natrosol Plus 330 CS) | | | 0.1 | | | |
| NaOH 45% strength solution in water | | 0.3 | | 0.1 | 0.7 | |
| EDTA solution | | 1 | | | 1 | |
| Water | ad 100 | ad 100 | ad 100 | ad 100 | ad 100 | ad 100 |

What is claimed is:

1. A Pickering emulsion, said Pickering emulsion being a finely dispersed water-in-oil or oil-in water system, said Pickering emulsion comprising:
   a) an oil phase;
   b) an aqueous phase;
   c) microfine particles, said microfine particles being metal oxides:
      i) having an average particle size of less than 200 nm;
      ii) being dispersible both in water and in oil;
      iii) having both hydrophilic and lipophilic properties resulting in amphiphilic character;
   d) one or more non-amphiphilic metal oxide pigments; and
   e) at most 0.5% by weight of one or more emulsifiers.

2. Pickering emulsions according to claim 1, which is emulsifier-free.

3. Pickering emulsions according to claim 1, wherein the content of the amphiphilic metal oxide microfine particles is between 0.1% by weight and 30% by weight, based on the total weight of the preparations.

4. Pickering emulsions according to claim 1, wherein the particle diameter of the amphiphilic metal oxide microfine particles is between 5 nm and 100 nm.

5. Pickering emulsions according to claim 1, wherein the amphiphilic metal oxide microfine particles have been surface-treated to repel water, where the amphiphilic character of the particles is formed or retained.

6. Pickering emulsions according to claim 1, wherein the total amount of non-amphiphilic pigments in the finished cosmetic or dermatological preparations is chosen to be less than 20% by weight based on the total weight of the preparations.

7. Pickering emulsion according to claim 6, wherein the total amount of non-amphiphilic pigments in the emulsion is between 0.5 and 10% by weight based on the total weight of the emulsion.

8. Pickering emulsion according to claim 1, wherein the total amount of non-amphiphilic pigment(s) is/are hydrophobic or hydrophobically coated metal oxides.

9. Pickering emulsion according to claim 8, wherein the total amount of non-amphiphilic pigment(s) is/are hydrophobic or hydrophobically coated titanium dioxides.

10. Pickering emulsions according to claim 1, wherein the non-amphiphilic pigment(s) is/are hydrophilic or hydrophilically coated metal oxides.

11. Pickering emulsions according to claim 10, characterized in that the non-amphiphilic pigment(s) is/are hydrophilic or hydrophilically coated titanium dioxides.

12. Sunscreen preparations based on Pickering emulsions according to claim 1.

13. A method of caring for the skin, said method comprising applying to skin an emulsion according to any one of claims 1–11 or a sunscreen preparation according to claim 1.

14. A method of increasing the UV protection performance of a cosmetic or dermatological Pickering emulsion comprising of:
   a) an oil phase;
   b) an aqueous phase;
   c) microfine particles, said microfine particles being metal oxides:
      i) having an average particle size of less than 200 nm;
      ii) being dispersible both in water and in oil;
      iii) having both hydrophilic and lipophilic properties resulting in amphiphilic character; and
   d) at most 0.5% by weight of one or more emulsifiers,
   said method comprising incorporating in said Pickering emulsion at least one type of non-amphiphilic metal oxide pigments.

15. The method according to claim 14, wherein the at least one type of non-amphiphilic metal oxide pigment(s) is/are hydrophobic or hydrophobically coated metal oxide(s).

16. The method according to claim 15, wherein the hydrophobic or hydrophobically coated metal oxide(s) is/are hydrophobic or hydrophobically coated titanium dioxide(s).

17. The method according to claim 14, wherein the at least one type of non-amphiphilic metal oxide pigment(s) is/are hydrophilically or hydrophilically coated metal oxide(s).

18. The method according to claim 17, wherein the hydrophobic or hydrophobically coated metal oxide(s) is/are hydrophilic or hydrophilically coated titanium dioxide(s).

* * * * *